US009428796B2

(12) United States Patent
Nakata (10) Patent No.: US 9,428,796 B2
(45) Date of Patent: Aug. 30, 2016

(54) METHOD FOR DETECTING A TARGET PARTICLE (71) Applicant: OLYMPUS CORPORATION, Tokyo (JP)

(72) Inventor: Hidetaka Nakata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/322,010

(22) Filed: Jul. 2, 2014

(65) Prior Publication Data

US 2014/0329709 A1 Nov. 6, 2014

Related U.S. Application Data (63) Continuation of application No. PCT/JP2012/081350, filed on Dec. 4, 2012.

(30) Foreign Application Priority Data

Feb. 22, 2012 (JP) .................................. 2012-036234

(51) Int. Cl.
*C12Q 1/68* (2006.01)
*C40B 30/04* (2006.01)
*G01N 21/64* (2006.01)

(52) U.S. Cl.
CPC ............ *C12Q 1/682* (2013.01); *G01N 21/6428* (2013.01); *G01N 21/6458* (2013.01)

(58) Field of Classification Search
CPC ............. C12Q 1/682; G01N 21/6458; G01N 21/6428; G01N 21/6486
See application file for complete search history.

(56) References Cited

U.S. PATENT DOCUMENTS

| | | | |
|---|---|---|---|
| 4,251,733 A | 2/1981 | Hirleman, Jr. | |
| 4,421,860 A | 12/1983 | Elings et al. | |
| 5,308,990 A | 5/1994 | Takahashi et al. | |
| 5,547,849 A | 8/1996 | Baer et al. | |
| 5,866,336 A | 2/1999 | Nazarenko et al. | |
| 6,280,960 B1 | 8/2001 | Carr | |
| 6,376,843 B1 | 4/2002 | Palo | |
| 6,388,746 B1 | 5/2002 | Eriksson et al. | |
| 6,388,788 B1 | 5/2002 | Harris et al. | |
| 6,400,487 B1 | 6/2002 | Harris et al. | |
| 6,403,338 B1 | 6/2002 | Knapp et al. | |
| 6,495,676 B1 | 12/2002 | Wood et al. | |
| 6,710,871 B1 | 3/2004 | Goix | |
| 6,782,297 B2 | 8/2004 | Tabor | |
| 6,856,391 B2 | 2/2005 | Garab et al. | |
| 6,927,401 B1 | 8/2005 | Palo | |
| 8,284,484 B2 | 10/2012 | Hoult et al. | |
| 2001/0035954 A1 | 11/2001 | Rahn et al. | |
| 2002/0008211 A1 | 1/2002 | Kask | |
| 2002/0036775 A1 | 3/2002 | Wolleschensky et al. | |
| 2003/0036855 A1 | 2/2003 | Harris et al. | |
| 2003/0218746 A1 | 11/2003 | Sampas | |
| 2004/0022684 A1 | 2/2004 | Heinze et al. | |
| 2004/0051051 A1 | 3/2004 | Kato et al. | |
| 2004/0150880 A1 | 8/2004 | Nakata et al. | |
| 2004/0152118 A1 | 8/2004 | Van Atta et al. | |
| 2005/0260660 A1 | 11/2005 | van Dongen et al. | |
| 2005/0277134 A1 | 12/2005 | Okano et al. | |
| 2006/0008799 A1 | 1/2006 | Cai et al. | |
| 2006/0078998 A1 | 4/2006 | Puskas et al. | |
| 2006/0158721 A1 | 7/2006 | Nakata et al. | |
| 2006/0256338 A1 | 11/2006 | Gratton et al. | |
| 2007/0231808 A1 | 10/2007 | Gouda et al. | |
| 2008/0052009 A1 | 2/2008 | Chiu et al. | |
| 2008/0158561 A1 | 7/2008 | Vacca et al. | |
| 2009/0159812 A1 | 6/2009 | Livingston | |

(Continued)

FOREIGN PATENT DOCUMENTS

CN 103620389 A 3/2014
EP 1 906 172 A1 4/2008

(Continued)

OTHER PUBLICATIONS

International Search Report, dated Mar. 5, 2013, issued in corresponding application No. PCT/JP2012/081350.
Takasugi, M., et al., "Sequence-specific photo-induced cross-linking of the two strands of double-helical DNA by a psoralen covalently linked to a triple helix-forming oligonucleotide", Proc. Natl. Acad. Sci. USA, Jul. 1991, vol. 88, pp. 5602-5606.
European Communication Pursuant to Article 94(3) EPC dated Nov. 20, 2014, issued in related European Patent Application No. 11812369.4 (6 pages).

(Continued)

*Primary Examiner* — Katherine Salmon
(74) *Attorney, Agent, or Firm* — Westerman, Hattori, Daniels & Adrian, LLP (57) ABSTRACT

The present invention provides a method for indirectly and with high sensitivity detecting a particle dispersed and moving randomly in a solution using a luminescent probe. In the present invention, (a) a solution is prepared that contains a target particle and one or more types of a luminescent probe that directly or indirectly binds to the target particle, (b) a complex is formed that contains the target particle and the luminescent probe in the solution, (c) the complex is recovered by separating luminescent probe not bound to the target particle from the solution containing the complex, followed by (d) dissociating the luminescent probe from the recovered complex and mutually separating and separately recovering the free luminescent probe and target particle, (e) again binding a luminescent probe to the recovered target particle followed by dissociating the luminescent probe and mutually separating and recovering free luminescent probe and the target particle are repeated, followed by preparing a single measurement sample solution containing the total amount of the recovered free luminescent probe, and (f) the number of molecules of the luminescent probes in the measurement sample solution is calculated.

11 Claims, 2 Drawing Sheets

(56) References Cited

U.S. PATENT DOCUMENTS

| | | |
|---|---|---|
| 2010/0033718 A1 | 2/2010 | Tanaami |
| 2010/0177190 A1 | 7/2010 | Chiang et al. |
| 2010/0202043 A1 | 8/2010 | Ujike |
| 2010/0301231 A1 | 12/2010 | Yamaguchi |
| 2010/0323350 A1 | 12/2010 | Gordon et al. |
| 2011/0312841 A1 | 12/2011 | Silverbrook et al. |
| 2014/0162378 A1* | 6/2014 | Hanashi ............ G01N 21/6408 436/501 |

FOREIGN PATENT DOCUMENTS

| | | |
|---|---|---|
| EP | 2216338 A1 | 8/2010 |
| EP | 2522988 A1 | 11/2012 |
| EP | 2543989 A1 | 1/2013 |
| EP | 2543990 A1 | 1/2013 |
| EP | 2584343 A1 | 4/2013 |
| EP | 2818850 A1 | 12/2014 |
| JP | 04501956 A | 4/1992 |
| JP | 04337446 A | 11/1992 |
| JP | 06113896 A | 4/1994 |
| JP | 2000-106876 A | 4/2000 |
| JP | 2002-507762 A | 3/2002 |
| JP | 2002-543414 A | 12/2002 |
| JP | 2004-506192 A | 2/2004 |
| JP | 2004-121231 A | 4/2004 |
| JP | 2004-187607 A | 7/2004 |
| JP | 2005-098876 A | 4/2005 |
| JP | 2005-099662 A | 4/2005 |
| JP | 2005-308412 A | 11/2005 |
| JP | 2006-333739 A | 12/2006 |
| JP | 2007-020565 A | 2/2007 |
| JP | 4023523 B | 12/2007 |
| JP | 2008-058285 A | 3/2008 |
| JP | 2008-116440 A | 5/2008 |
| JP | 2008-536093 A | 9/2008 |
| JP | 2008-292371 A | 12/2008 |
| JP | 2008-298743 A | 12/2008 |
| JP | 2009-145242 A | 7/2009 |
| JP | 2009-250721 A | 10/2009 |
| JP | 2009-281831 A | 12/2009 |
| JP | 2009-288161 A | 12/2009 |
| JP | 2010-019553 A | 1/2010 |
| JP | 2010-190730 A | 9/2010 |
| JP | 2011-002415 A | 1/2011 |
| JP | 2011-033613 A | 2/2011 |
| JP | 2011-036150 A | 2/2011 |
| JP | 2011-508219 A | 3/2011 |
| WO | 88/02785 A2 | 4/1988 |
| WO | 90/06042 A2 | 6/1990 |
| WO | 92/22671 A1 | 12/1992 |
| WO | 98/16814 A1 | 4/1998 |
| WO | 99/47963 A | 9/1999 |
| WO | 00/52451 A1 | 9/2000 |
| WO | 00/66985 A1 | 11/2000 |
| WO | 00/71991 A1 | 11/2000 |
| WO | 02/12864 A1 | 2/2002 |
| WO | 2004/020675 A2 | 3/2004 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008/080417 A1 | 7/2008 |
| WO | 2009/066447 A1 | 5/2009 |
| WO | 2009/117033 A2 | 9/2009 |
| WO | 2010/056579 A1 | 5/2010 |
| WO | 2011/108369 A1 | 9/2011 |
| WO | 2011/108370 A1 | 9/2011 |
| WO | 2011/108371 A1 | 9/2011 |
| WO | 2012/014778 A1 | 2/2012 |

OTHER PUBLICATIONS

Shuming N. et al., "Real-Time Detection of Single Molecules in Solution by Confocal Fluorescence Microscopy", Analytical Chemistry, American Chemical Society, vol. 67, No. 17, pp. 2849-2857, (1995), European Communication dated Nov. 20, 2014.
U.S. Non-Final Office Action dated Mar. 4, 2015, issued in U.S. Appl. No. 14/172,295. (39 pages).
U.S. Office Action dated Apr. 13, 2015, issued in U.S. Appl. No. 13/746,968 (19 pages).
Office Action dated Apr. 20, 2015, issued in Chinese Patent Application No. 201280041270.6 with English translation (11 pages).
Extended European Search Report dated May 20, 2015, issued in Patent Application No. 12828423.9 (18 pages).
Communication pursuant to Article 94(3) dated May 13, 2015, issued in European Patent Application No. 11 812 369.4 (5 pages).
Extended European Search Report dated Oct. 20, 2014, issued in related EP Application No. 12770835.2 (10 pages).
Notice of Reasons for Rejection dated May 19, 2015, issued in corresponding Japanese Patent Application No. 2012-526460 with English translation (8 pages).
Hebert et al., "Spatiotemporal Image Correlation Spectroscopy (STICS) Theory, Verification, and Application to Protein Velocity Mapping in Living CHO Cells", Biophysical Journal, May 2005, vol. 88, No. 5, pp. 3601-3614, Extended European Search Report dated Mar. 26, 2015 (14 pages).
Extended European Search Report dated Mar. 26, 2015, issued in corresponding EP Patent Application No. 12821897.1 (13 pages).
Office Action dated Mar. 25, 2015, issued in Chinese Patent Application No. 201180036710.4, with English translation (8 pages).
Park, Mira et al., "Counting the Number of Fluorophores Labeled in Biomolecules by Observing the Fluorescence-Intensity Transient of a Single Molecule", Bulletin of the Chemical Society of Japan, Aug. 30, 2005, vol. 78, No. 9, p. 1612-1618.
U.S. Office Action dated Apr. 2, 2013, issued in related U.S. Appl. No. 13/596,280 (7 pages).
Kask, Peet et al., "Two-Dimensional Fluorescence Intensity Distribution Analysis: Theory and Applications", Biophysical Journal, Apr. 2000, vol. 78, p. 1703-1713.
Chinese Office Action dated Aug. 13, 2013, issued in related Chinese application No. 201180011655.3; w/ English Translation (16 pages).
International Search Report dated Mar. 29, 2011, issued in related PCT/JP2011/053483.
International Preliminary Report on Patentability (PCT/IPEA/409) Mar. 30, 2012, issued in related PCT/JP2011/053483.
Chinese Office Action dated Aug. 9, 2013, issued in related Chinese application No. 201180011640.7; w/ English Translation (16 pages).
International Search Report dated Mar. 29, 2011, issued in related PCT/JP2011/053482.
International Preliminary Report on Patentability (PCT/IPEA/409) dated Mar. 30, 2012, issued in related PCT/JP2011/053482.
Sasaki, Shigeki, "Creation of Functional Recognition Molecules for Chemical Modification of Gene Expression", Yakugaku Zasshi, the Pharmaceutical Society of Japan, 2002, vol. 122, No. 12, p. 1081-1093.
Chinese Office Action dated Feb. 7, 2013, issued in related Chinese application No. 201180011644.5; w/ English Translation (19 pages).
Extended European Search Report dated Mar. 28, 2013, issued in related EP application No. 11750481.1.
International Search Report dated Mar. 29, 2011, issued in related PCT/JP2011/053481.
International Preliminary Report on Patentability (PCT/IPEA/409) dated Jun. 15, 2012 issued in related PCT/JP2011/053481.
Goodwin, Peter et al., "Rapid Sizing of Individual Fluorescently Stained DNA Fragments by Flow Cytometry", Nucleic Acids Research, 1993, vol. 21, No. 4, p. 803-806.
Keller, Richard et al., "Single-Molecule Fluorescence Analysis in Solution", Applied Spectroscopy, 1996, vol. 50, No. 7, p. 12A-32A.
Lee, Yuan-Hsiang et al., "Laser-Induced Fluorescence Detection of a Single Molecule in a Capillary", Analytical Chemistry, Dec. 1, 1994, vol. 66, No. 23, p. 4142-4149.

(56) References Cited

OTHER PUBLICATIONS

Li, Haitao et al., "Ultrasensitive Coincidence Fluorescence Detection of Single DNA Molecules", Analytical Chemistry, Apr. 1, 2003, vol. 75, No. 7, p. 1664-1670.

Nie, Shuming et al., "Probing Individual Molecules with Confocal Fluorescence Microscopy", Science, Nov. 11, 1994, vol. 266, p. 1018-1021.

Tahari, Abdel. "Fluorescence Correlation Spectroscopy: Ultrasensitive Detection in Clear and Turbid Media", University of Illinois, 2006, p. 1-88.

Wu, Alan et al., "Development and Preliminary Clinical Validation of a High Sensitivity Assay for Cardiac Troponin Using a Capillary Flow (Single Molecule) Fluorescence Detector", Clinical Chemistry, 2006, vol. 52, No. 11, p. 2157-2159.

Itoh et al., "A New Method for Detection of Influenza Viruses by Single Particle-Recognition Based on the Principle of Fluorescence Correlation Spectroscopy", Chemistry and Biology, 2009, vol. 47, No. 12, p. 823-830; with English summary.

Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.

U.S. Office Action dated Oct. 4, 2013, issued in related U.S. Appl. No. 13/596,243 (7 pages).

Japanese Office Action dated Dec. 18, 2012, issued in related JP application No. 2012-503060; w/ English Translation (6 pages).

Yoshimura, Yoshinaga et al., "Development of Template-Directed Reversible DNA Photocrosslinking", Nucleic Acids Symposium Series, 2008, vol. 10, No. 52, p. 423-424.

Yoshimura, Yoshinaga et al., "Ultrafast Reversible Photo-Cross-Linking Reaction: Toward in Situ DNA Manipulation", Organic Letters, 2008, vol. 10, No. 15, p. 3227-3230.

U.S. Notice of Allowance dated Jun. 19, 2013, issued in co-pending U.S. Appl. No. 13/596,280.

Kask, Peet et al. "Fluorescence-Intensity Distribution Analysis and its Application in Biomolecular Detection Technology", PNAS, Nov. 23, 1999, vol. 96, No. 24, p. 13756-13761.

Kinjo, M. "Single Molecule Detection by Fluorescence Correlation Spectroscopy", Proteins, Nucleic Acids and Enzymes, 1999, vol. 44, No. 9, p. 1431-1438.

Meyer-Almes, F. J. "A New Method for Use in Molecular Diagnostics and High Throughput Pharmaceutical Screening based on Fluorescence Correlation Spectroscopy", Nanoparticle Immunoassays, R. Ridger, edit., Springer, Berlin, 2000, p. 204-224.

Kato, N. et al., "A Single Molecule Analyzer that Enables New Analysis of DNA and Protein Interactions", Gene Medicine, 2002, vol. 6, No. 2, p. 271-277 with English summary.

Sando, Shinsuke et al., "Quencher as Leaving Group: Efficient Detection of DNA-Joining Reactions", Journal of the American Chemical Society, 2002, vol. 124, No. 10, p. 2096-2097.

International Search Report dated Sep. 20, 2011, issued in related PCT/JP2011/066576 (6 pages).

U.S. Office Action dated Feb. 20, 2014, issued in related U.S. Appl. No. 13/746,968 (11 pages).

U.S. Notice of Allowance dated Mar. 27, 2013, issued in related U.S. Appl. No. 13/597,825 (8 pages).

U.S. Office Action dated May 22, 2014, issued in related U.S. Appl. No. 13/746,968 (10 pages).

International Search Report dated Apr. 23, 2013, issued in related PCT/JP2013/053080 (4 pages).

International Search Report dated Jul. 24, 2012, issued in related PCT/JP2012/060137 (6 pages).

International Search Report dated Aug. 7, 2012, issued in related PCT/JP2012/066576 (4 pages).

U.S. Office Action dated Jan. 3, 2013, issued in co-pending U.S. Appl. No. 13/597,825.

Chinese Office Action dated Jul. 14, 2014, issued in related Chinese application No. 201180036710.4; w/ English Translation (12 pages).

U.S. Notice of Allowance dated Dec. 24, 2013, issued in related U.S. Appl. No. 13/596,243 (13 pages).

Advisory Action mailed Jan. 5, 2016, issued in U.S. Appl. No. 14/172,295.

Advisory Action mailed Feb. 23, 2016, issued in U.S. Appl. No. 13/746,968.

Official Notice dated Nov. 30, 2015, issued in European application No. 11812369.4.

Prasad V et al. "Topical Review; Confocal microscopy of colloids", Journal of Physics: Condensed Matter, Institute of Physics Publishing, Bristol, GB, vol. 19, No. 11, Mar. 21, 2007, p. 113102.

Extended European Search Report issued Feb. 16, 2016 in EP 13764425.8.

Non-Final Office Action dated Aug. 20, 2015, issued U.S. Appl. No. 14/172,295 (14 pages).

Final Office Action dated Sep. 28, 2015, issued in U.S. Appl. No. 13/746,968 (24 pages).

\* cited by examiner

METHOD FOR DETECTING A TARGET PARTICLE

The present application is a U.S. continuation application based on the PCT International Patent Application, PCT/JP2012/081350, filed on Dec. 4, 2012; the content of which is incorporated herein by reference.

BACKGROUND OF THE INVENTION

1. Field of the Invention

The present invention relates to a method for detecting a target particle using an optical system of a confocal microscope or multi-photon microscope and the like capable of detecting light from a microregion in a solution.

2. Description of the Related Art

Due to progress made in the field of optical measurement technology in recent years, it has become possible to detect and measure feint light at the level of a single photon or single fluorescent molecule using the optical system of a confocal microscope and ultra-high-sensitivity photodetection technology capable of performing photon counting (detecting individual photons). Therefore, various devices or methods have been proposed that detect interactions between molecules such as biomolecules or coupling and dissociation reactions between molecules using such feint light measurement technology. In particular, according to a method such as fluorescence correlation spectroscopy (FCS) or fluorescence intensity distribution analysis (FIDA) that uses a technology for measuring fluorescence of a microregion (confocal region where laser light of a microscope is focused; referred to as confocal volume) using the optical system of a confocal microscope and photocounting technology, the sample required for measurement is only required to be at an extremely low concentration and in an extremely small amount in comparison with that used in the past (since the amount used for a single measurement is roughly only several tens of microliters), and measurement time is shortened considerably (measurement of a duration on the order of several seconds for a single measurement is repeated several times).

More recently, an optical analysis technology (scanning molecule counting method) employing a novel approach has been proposed that individually detects luminescent particles (particles that emit light) traversing a photodetection region in a sample solution in the form of a microregion while moving the location of the microregion using an optical system capable of detecting light from a microregion in a solution, such as the optical system of a confocal microscope or multi-photon microscope (see, for example, PCT International Publication No. WO 2011/108369; PCT International Publication No. WO 2011/108370; and PCT International Publication No. WO 2011/108371). More specifically, the scanning molecule counting method is a technique that enables counting of luminescent particles, or acquiring information relating to concentration or number density of luminescent particles in a sample solution, by detecting light emitted from the luminescent particles in a photodetection region to individually detect each of the luminescent particles in a sample solution while moving the location of the photodetection region of an optical system of a confocal microscope or multi-photon microscope in the sample solution using that optical system.

Since the photodetection mechanism per se of the scanning molecule counting method is composed so as to detect light from a photodetection region of a confocal microscope or multi-photon microscope in the same manner as in the case of optical analysis technologies such as FIDA, the amount of sample solution may also be an extremely small amount (such as roughly several tens of microliters) and only a short measurement time is required in the same manner as optical analysis technologies such as FIDA. On the other hand, the scanning molecule counting method differs from FIDA and the like, which requires statistical processing involving calculation of fluctuations in fluorescent intensity and the like, in that such statistical processing is not carried out. Consequently, optical analysis technology employing the scanning molecule counting method can be applied to sample solutions in which the number density or concentration of particles is considerably lower than the level required by optical analysis technologies such as FIDA. In other words, by detecting a target particle (an observation target particle) in a sample solution labeled with a luminescent probe using the scanning molecule counting method, the status or properties of the target particle can be detected and analyzed even in the case the concentration or number density of the target particles in the sample solution is extremely low (see, for example, PCT International Publication No. WO 2012/014778).

SUMMARY OF THE INVENTION

As a result of conducting extensive studies to solve the aforementioned problems, the inventors of the present invention found that a plurality of signal sources (luminescent probes) can be generated from a single molecule of a target particle by repeating a plurality of times operations consisting of: recovering a luminescent probe bound to a target particle by separating from free luminescent probe, and then recovering the luminescent probe by dissociating from the target particle, thereby leading to completion of the present invention.

Namely, the method for detecting target particles of the present invention consists of that described in (1) to (11) below.

(1) A method for indirectly detecting a particle dispersed and moving randomly in a solution using a luminescent probe, that includes carrying out:

(a) preparing a solution containing a target particle to be detected and one or more types of a luminescent probe that directly or indirectly binds to the target particle;

(b) forming a complex containing the target particle and the luminescent probe in the solution;

(c) removing luminescent probe not bound to the target particle from the solution containing the complex, thereby recovering the complex;

(d) dissociating the luminescent probe from the recovered complex and separating the free luminescent probe and the target particle, thereby separately recovering the free luminescent probe and the target particle;

(e) repeating one or more times a cycle consisting of the following operations:

(a') preparing a solution by newly adding the luminescent probe to the target particle recovered by separating from free luminescent probe in the (d);

(b') forming a complex containing the target particle and the luminescent probe in the solution following the (a');

(c') separating luminescent probes not bound to the target particle, thereby recovering the complex from the solution, following the (b'); and, (d') dissociating the luminescent probe from the complex recovered in the (c') followed by mutually separating and recovering free luminescent probes and the target particle;

followed by preparing a single measurement sample solution containing the total amount of free luminescent probe recovered in the (d) and the (d'); and, (f) calculating the number of molecules of the luminescent probes in the measurement sample solution by a method consisting of detecting light emitted from the luminescent probe in a photodetection region of an optical system of a confocal microscope or multiphoton microscope while moving the location of the photodetection region in the measurement sample solution using the optical system.

(2) The method for detecting a target particle of (1) above, wherein dissociation of the luminescent probe from the complex in the (d') is carried out in a solution containing free luminescent probes recovered in the (d).

(3) The method for detecting a target particle of (1) above, wherein after mixing the entirety of the solutions containing free luminescent probes recovered in each of the (d) and the (d') in the (e), a single measurement sample solution is prepared by carrying out concentration treatment.

(4) The method for detecting a target particle of any of (1) to (3) above, wherein a separation probe that binds to the target particle independent of the luminescent probe is further added to the solution in the (a),
a complex formed in the (b) and the (b') contains the target particle, the luminescent probe and the separation probe, and
the target particle in the state of a complex bound to the separation probe in the (d) and the (d') is recovered by separating from free luminescent probes.

(5) The method for detecting a target particle of any of (1) to (4) above, wherein the target particle is a nucleic acid molecule.

(6) The method for detecting a target particle of (4) above, wherein the target particle is a nucleic acid molecule, and the Tm value of a complex of the target particle and the separation probe is higher than the Tm value of a complex of the target particle and the luminescent probe.

(7) The method for detecting a target particle of (6) above, wherein dissociation of the luminescent probe from the complex is carried out in the (d) and the (d') by making the temperature of a solution containing the complex higher than the Tm value of a complex of the target particle and the luminescent probe and lower than the Tm value of a complex of the target particle and the separation probe.

(8) The method for detecting a target particle of any of (4) to (7) above, wherein the luminescent probe is a naturally-occurring oligonucleotide having a luminescent substance bound thereto and the separation probe is an oligonucleotide composed of peptide nucleic acids.

(9) The method for detecting a target particle of (4) or (5) above, wherein forming of at least one covalent bond between the target particle and the separation probe in the complex formed in the (b) is carried out prior to the (d).

(10) The method for detecting a target particle of any of (4) to (9) above, wherein recovery of the complex in the (c) and recovery of free luminescent probes in the (d) and the (d') are carried out by solid-liquid separation treatment using a solid phase carrier that directly or indirectly binds to the separation probe.

(11) The method for detecting a target particle of any of (1) to (10) above, wherein the one or more types of luminescent probe are two or more luminescent probes.

BRIEF DESCRIPTION OF THE REFERENCE SYMBOLS

1: target particle, 2: luminescent probe, 3: separation probe, 4: solid phase carrier

DETAILED DESCRIPTION OF THE PREFERRED EMBODIMENTS

The method for detecting a target particle of the present invention (to also be referred to as the "detection method of the present invention") is characterized by having the following operations (a) to (f) in a method for indirectly detecting a target particle dispersed and moving randomly in a solution using a luminescent probe:

(a) preparing a solution containing a target particle to be detected and one or more types of a luminescent probe that directly or indirectly binds with the target particle;

(b) forming a complex containing the target particle and the luminescent probe in the solution;

(c) removing luminescent probes not bound to the target particle from the solution containing the complex, thereby recovering the complex; and, (d) dissociating the luminescent probe from the recovered complex and separating the free luminescent probe and the target particle, thereby separately recovering the free luminescent probe and the target particle;

(e) repeating one or more times a cycle consisting of the following operations:

(a') preparing a solution by newly adding the luminescent probe to the target particle recovered by separating from free luminescent probe in the (d);

(b') forming a complex containing the target particles and the luminescent probe in the solution following the (a');

(c') separating luminescent probes not bound to the target particle following the (b'), thereby recovering the complex from the solution; and, (d') dissociating the luminescent probe from the complex recovered in the (c') followed by mutually separating and recovering free luminescent probes and the target particle;

followed by preparing a single measurement sample solution containing the total amount of free luminescent probes recovered in the (d) and the (d'); and, (f) calculating the number of molecules of the luminescent probes in the measurement sample solution by a method consisting of detecting light emitted from the luminescent probe in a photodetection region of an optical system of a confocal microscope or multiphoton microscope while moving the location of the photodetection region in the measurement sample solution using the optical system.

In the present invention and description of the present application, the phrase, "(a) particle(s) dispersed and moving randomly in a solution", refers to (a) particle(s) such as (an) atom(s), (a) molecule(s) or (an) aggregate(s) thereof dispersed or dissolved in a solution (and may be a particle that emit light or a particle that does not emit light) that move about freely by Brownian movement in a solution without being immobilized on a substrate and the like.

The target particle to be detected by the detection method of the present invention refers to a particle that is dispersed and moving randomly in a solution, and may be an arbitrary particle without any particular limitations thereon. Examples of a target particle includes a biomolecule such as a protein, peptide, nucleic acid, nucleic acid-like substance, lipid, saccharide, amino acid, or an aggregate thereof, a particulate biological target such as virus or bacteria, and a non-biological particle (such as an atom, a molecule, a micelle or a metal colloid). Nucleic acid may be DNA or RNA, or may be artificially amplified substances in the manner of cDNA. Examples of nucleic acid-like substance include substances in which side chains and the like of naturally-occurring nucleotide (nucleotide present in nature) in the manner of DNA or RNA have been modified by functional groups such as an amino group, and a substance that has been labeled with a protein or low molecular weight compound and the like. Specific examples of nucleic acid-like substances include bridged nucleic acid (BNA), nucleotide in which an oxygen atom at position 4' of a naturally-occurring nucleotide has been substituted with a sulfur atom, nucleotides in which a hydroxyl group at position 2' of a naturally-occurring nucleotide has been substituted with a methoxy group, hexitol nucleic acid (HNA) and peptide nucleic acid (PNA).

The target particle in the detection method of the present invention may be a nucleic acid molecule or a nucleic acid-like substance (and in the present description, these may be referred to as "a nucleic acid molecule and the like"). The nucleic acid molecule or nucleic acid-like substance may be a double-stranded nucleic acid molecule or single-stranded nucleic acid molecule. Specific examples thereof include a nucleic acid molecule having a base sequence present in the chromosome of an animal or plant or in the gene of a bacterium or virus, and a nucleic acid molecule having an artificially designed base sequence. Among these, the target particle is preferably micro RNA, siRNA, mRNA, hnRNA, genomic DNA, synthetic DNA obtained by PCR or other amplification, or cDNA synthesized from RNA using a reverse transcriptase.

In addition, a luminescent probe used in the present embodiment is a substance that specifically or non-specifically binds (with binding to include absorption, and to apply similarly hereinafter) to a target particle, and there are no particular limitations thereon provided it emits light that can be detected in the case of using the optical system of a confocal microscope or multi-photon microscope. For example, the luminescent probe may be that in which a luminescent substance is bound to a substance that specifically or non-specifically binds to a target particle. Although the luminescent substance is typically a fluorescent substance, it may also be a substance that emits light by phosphorescence, chemiluminescence, bioluminescence or light scattering. There are no particular limitations on the fluorescent substance provided it is a substance that releases fluorescence as a result of being irradiated with light of a specific wavelength, and can be used by suitably selecting from among fluorescent dyes used in FCS or FIDA and the like.

In addition, the luminescent probe used in the present invention may be that which binds directly to a target particle or that which binds indirectly to a target particle. For example, in the case the target particle is a nucleic acid molecule or nucleic acid-like substance, examples of the luminescent probe that bind directly to a target particle include that in which a luminescent substance such as a fluorescent substance is bound to an oligonucleotide that hybridizes with the target particle, a nucleic acid-binding substance bound with a luminescent substance such as a fluorescent substance, and a dye molecule that binds to nucleic acid. The oligonucleotide may be DNA, RNA or an artificially amplified substance in the manner of cDNA, or a substance that contains a portion or all of a nucleic acid-like substance capable of forming a nucleotide chain and base pairs in the same manner as naturally-occurring nucleic acid bases. In addition, in the case the target particle is a protein, a substance in which an antigen or antibody to the target particle or a ligand or receptor for the target particle is labeled with a luminescent substance such as a fluorescent substance can be used as a luminescent probe that binds directly to a target particle. Furthermore, binding of a luminescent substance to a substance that specifically or non-specifically binds or absorbs to a target particle such as a nucleic acid or protein can be carried out by ordinary methods.

Although the luminescent probe used in the present embodiment may be a substance that non-specifically binds to a target particle, from the viewpoint of accuracy of detection and quantitative determination of a target particle, the probe can be a substance that binds specifically to the target particle. Furthermore, the luminescent probe that specifically binds to a target particle is only required to be a substance that selectively binds to the target particle rather than binding to other substances having physical or chemical properties similar to those of the target particle, and is not required to be a substance that does not bind at all to substances other than the target particle. Thus, in the case the target particle is a nucleic acid molecule, for example, an oligonucleotide labeled with a luminescent substance used as a luminescent probe may have a base sequence that is completely complementary to the base sequence of the target particle, or may have a base sequence that contains one or several base mismatches with a partial base sequence of the target particle.

In the present invention, a single molecule of a luminescent probe may be bound to a single molecule of a target particle, or a plurality of molecules of a luminescent probe may be bound to a single molecule of a target particle. In the case of a plurality of luminescent probes being bound to a single molecule of a target particle, these luminescent probes can be designed so as to bind to a target particle mutually independently thereof. A plurality of molecules of one type of luminescent probe may be bound to a single molecule of a target particle, or a plurality of types of luminescent probes may be bound to a single molecule of a target particle. In the case of binding a plurality of types of luminescent probes, although each luminescent probe may be a probe labeled with a substance having mutually different luminescence properties of the released light, from the viewpoint of increasing detection sensitivity when a low concentration of detection target is bound to the luminescent probe, a probe can be one bound with the same type of luminescent substance.

More specifically, in (a), a target particle and a luminescent probe are added to a solvent to prepare a solution containing both. There are no particular limitations on the solvent provided it is a solvent that does not impair the properties of the target particle and luminescent probe. Although water is typically used for the solvent, an organic solvent such as formaldehyde or other arbitrary solvent may be used. More specifically, the solvent can be used by suitably selecting from among buffers commonly used in the art. Examples of these buffers include Tris buffers or phosphate buffers such as phosphate-buffered saline (PBS, pH 7.4).

Although there are no particular limitations on the concentration of the luminescent probe added to the solution, a solution containing the luminescent probe and the target particle may be prepared so that the concentration of the luminescent probe is higher than the predicted concentration of the target particle in order to enhance detection sensitivity of the target particle in the detection method. In the method of the present invention, free luminescent probe not bound to target particles is removed from the luminescent probe bound to the target particles in the subsequent (c). Consequently, the target particle can be accurately detected even in the case of having added an excess amount of the luminescent probe in (a).

Next, a complex containing the aforementioned target particle and the aforementioned luminescent probe is formed in the aforementioned solution in (b). In the case of being able to bind the target particle and the luminescent probe by simply having them both present in the same solution, a complex containing the target particle and the luminescent probe can be formed in the solution simply by incubating the solution for a prescribed amount of time as necessary after having prepared the solution containing both.

On the other hand, in the case the target particle and the luminescent probe are nucleic acid molecules or nucleic acid-like substances having a double-stranded structure, the target particle and luminescent probe may be associated after having denatured the nucleic acid molecules and the like in the solution. Furthermore, "denaturing nucleic acid molecules and the like" refers to dissociating base pairs within a molecule such as a nucleic acid molecule. For example, this refers to denaturing a double-stranded nucleic acid molecule to a single-stranded nucleic acid molecule. Furthermore, in the case the luminescent probe is an oligonucleotide containing a nucleic acid like-substance such as PNA, even if the target particle is a double-stranded nucleic acid molecule, a complex containing the luminescent probe and the target particle may be able to be formed without having to carry out special denaturation treatment, and in this case, the complex can be formed without having to denature the nucleic acid molecule and the like.

Examples of denaturation treatment carried out on nucleic acid molecules and the like include denaturation by high-temperature treatment (heat denaturation) and denaturation by low salt concentration treatment. In particular, one can choose heat denaturation since the effects on fluorescent substances or other luminescent substances are comparatively low and the procedure is simple. More specifically, in the case of heat denaturation, nucleic acid molecules and the like in a solution can be denatured by subjecting the solution to high-temperature treatment. In general, although nucleic acid molecules and the like can be denatured by warming at a temperature of 90° C. for DNA or 70° C. for RNA for several seconds to about 2 minutes, since the denaturing temperature varies according to the base length of the target particle in the form of a nucleic acid molecule and the like, the aforementioned warming temperature and warming time are not limited thereto provided denaturation is possible. On the other hand, denaturation by low salt concentration treatment can be carried out by, for example, adjusting the salt concentration of the solution to be sufficiently low by diluting with purified water and the like.

After having denatured as necessary, the target particle in the form of a nucleic acid molecule and the like and the luminescent probe in the aforementioned solution are associated to form a complex containing both. In the case of having carried out heat denaturation of nucleic acid molecules and the like, both the target particle and luminescent probe in the solution can be suitably associated by lowering the temperature of the solution to a temperature that allows the target particle and luminescent probe to specifically hybridize (specific association conditions) following heat denaturation. The temperature of the solution containing both may be lowered to a temperature range of ±3° C. of the Tm value of the region to be hybridized in the complex. In addition, in the case of having carried out denaturation by low salt concentration treatment, the target particle and luminescent probe in the solution can be suitably associated by raising the salt concentration of the solution to a concentration that allows specific hybridization between the target particles and luminescent probe by adding a salt solution and the like.

Furthermore, the temperature at which two single-stranded nucleic acid molecules are able to specifically hybridize can be determined from a melting curve of an association product of the target particle and luminescent probe. A melting curve can be determined by, for example, changing the temperature of a solution containing only the target particle and luminescent probe from a high temperature to a low temperature and measuring optical absorbance or fluorescence intensity of the solution. The temperature range from the temperature at which the two denatured single-stranded nucleic acid molecules begin to form an association product to the temperature at which the nucleic acid molecules have nearly completely formed an association product as determined from the resulting melting curve can be taken to be the temperature range over which both are able to specifically hybridize. The concentration at which two single-stranded nucleic acid molecules can specifically hybridize can be determined by similarly determining a melting curve by changing the salt concentration in the solution from a low concentration to a high concentration instead of changing the temperature.

In this manner, although specific association conditions vary for each type of target particle and luminescent probe and are determined experimentally, in the case the target particles are nucleic acid molecules and the like, the conditions can normally be substituted with melting temperature (Tm). For example, the Tm value of a region that hybridizes with a target particle (temperature at which 50% of double-stranded DNA dissociates to single-stranded DNA) can be calculated from base sequence information of the luminescent probe by using commonly used primer/probe design software and the like. Conditions in which the temperature is in the vicinity of the Tm value, and for example, conditions in which the temperature is within about ±3° C. of the Tm value, can be used as specific association conditions. More detailed specific association conditions can be determined by experimentally determining a melting curve at a temperature in the vicinity of the calculated Tm value.

In addition, in order to suppress non-specific hybridization, the temperature of the aforementioned solution may be lowered comparatively slowly when forming a complex. For example, after having denatured a nucleic acid molecule by making the temperature of the aforementioned solution to be 70° C. or higher, the liquid temperature of the solution can be lowered at a temperature lowering rate of at least 0.05° C./second.

In addition, in order to suppress non-specific hybridization, a surfactant, formamide, dimethylsulfoxide or urea and the like may be added to the aforementioned solution in advance. Only one type of these compounds may be added or two or more types may be added in combination. The addition of these compounds makes it possible to make it difficult for non-specific hybridization to occur in a comparatively low-temperature environment.

Following (b), (c) consists of removing luminescent probe not bound to the aforementioned target particle from the aforementioned solution containing the aforementioned complex, and recovering the aforementioned complex. In the method of the present invention that uses an optical analysis technology for individually detecting a target particle labeled with a luminescent probe, if light from free luminescent probe that has not formed a complex with the target particle ends up being detected without distinguishing from luminescent probe bound to the target particle, detection sensitivity of the target particle becomes poor. Therefore, in (c), the free luminescent probe and the like (substances present in the solution other than the complex) are removed from the aforementioned solution.

In (c), there are no particular limitations on the specific means used to remove luminescent probe not bound to target particle and recover the aforementioned complex, and can be suitably selected from among methods used to separate substances normally carried out in the art when physically separating a plurality of substances utilizing differences in size, molecular weight, affinity to an arbitrary substance or charged state and the like. Examples of these separation methods include procedures that include adsorption, extraction or washing. Specific examples include chromatography (such as hydrophilic/hydrophobic interaction chromatography, affinity chromatography or ion exchange chromatography), ultrafiltration, electrophoresis, phase separation, centrifugal separation, solvent extraction and filtration-adsorption.

In (c), the aforementioned complex can be recovered by removing luminescent probe not bound to the target particle utilizing a separation probe that binds to the target particle independently of the luminescent probe. More specifically, a separation probe is further added to the aforementioned solution in (a), and a complex containing the target particle, luminescent probe and separation probe is formed in (b). Next, in (c), luminescent probe not bound to the target particle is removed by selectively retaining the complex by utilizing interaction between the separation probe and other substances in the complex.

There are no particular limitations on the separation probe provided it is a substance that specifically or non-specifically binds (including adsorption, and to apply similarly hereinafter) to the target particle independently of the luminescent probe. Although the separation probe may be that which binds to the target particle indirectly by having another substance interposed there between, it may bind directly to the target particle. Examples of substances able to be used as a separation probe that bind directly to the target particle either specifically or non-specifically include those listed as examples in the previous explanation of the luminescent probe prior to being bound by a luminescent substance. For example, an oligonucleotide that hybridizes with the target particle serves as a separation probe in the case the target particle is a nucleic acid molecule and the like, while an antigen or antibody to the target particle or a ligand or receptor for the target particle serves as a separation probe in the case the target particle is protein.

The separation probe used in the present invention has a site that binds to a solid phase carrier and further binds directly or indirectly with the solid phase carrier in a state in which it is bound to target particle. In the case of using the separation probe, recovery of the complex in (c) and recovery of free luminescent probe in the subsequent (d) can be carried out more easily by solid-liquid separation treatment using a solid phase carrier that directly or indirectly binds to the separation probe.

There are no particular limitations on the form or material and so forth of the solid phase carrier used for the separation probe provided it is a solid provided with a site that binds to the separation probe. For example, the solid phase carrier may consist of particles such as beads that can be suspended in water and are capable of being separated from liquid by ordinary solid-liquid separation treatment, a membrane, a container or a chip substrate. Specific examples of solid phase carriers include magnetic beads, silica beads, agarose gel beads, polyacrylamide resin beads, latex beads, polystyrene and other plastic beads, ceramic beads, zirconia beads, silica membranes, silica filters and plastic plates.

For example, in the case the separation probe is an oligonucleotide, beads or filters capable of binding the oligonucleotide in a state in which a portion that hybridizes with a region other than the region that hybridizes with the target particle is exposed on the surface thereof can be used as a solid phase carrier. In addition, in the case the separation probe has biotin for the site that binds to the solid phase carrier, beads or filters that enable avidin or streptavidin to bind to the surface while retaining binding properties with biotin can be used as a solid phase carrier. In addition, in the case the site in the separation probe that binds to a solid phase carrier is glutathione, dinitrophenol (DNP), digoxigenin (Dig), digoxin, a sugar chain composed of two or more sugars, a polypeptide composed of four or more amino acids, an auxin, gibberellin, steroid, protein, hydrophilic organic compound, or analogue thereof; beads or filters having an antibody, antigen, ligand or receptor for these substances bound to the surface thereof can be used as a solid phase carrier. Furthermore, although the solid phase carrier may be that which binds non-specifically to the separation probe, it may bind specifically from the viewpoint of accurate detection and quantitative determination of target particles.

More specifically, a complex containing target particle, a luminescent probe and a separation probe in the aforementioned solution is bound to a solid phase carrier through the separation probe in the complex by contacting the solid phase carrier with the solution containing the complex and incubating as necessary. Subsequently, the complex bound to the solid phase carrier can be separated and recovered from luminescent probe not bound to the target particles present in a liquid phase, such as free luminescent probe, by subsequently carrying out solid-liquid separation treatment.

There are no particular limitations on the solid-liquid separation treatment provided a method is used that allows separation and recovery of the solid phase carrier in the solution from liquid components, and can be suitably selected from among known treatment methods used for solid-liquid separation treatment. For example, in the case the solid phase carrier consists of beads and the like, centrifugal separation treatment may be carried out on a suspension containing the solid phase carrier to precipitate the solid phase carrier followed by removing the supernatant, or the solution may be filtered using filter paper or a filtration filter and recovering the solid phase carrier remaining on the surface of the filter paper and the like. In addition, in the case the solid phase carrier consists of magnetic beads, a magnet may be brought in close proximity to a container containing the solution to cause the solid phase carrier to converge at the surface of the container closest to the magnet followed by removing the supernatant. In the case a container having an inner wall coated with a substance that binds to the separation probe is used for the solid phase carrier, a solution containing the aforementioned complex is poured into the container followed by discharging the liquid from the container after having incubated as necessary. Furthermore, in the case the solid phase carrier is a membrane or filter, binding between the solid phase carrier and the aforementioned complex as well as separation and recovery of the aforementioned complex from luminescent probe not bound to the target particles can be carried out in a single procedure by allowing a solution containing the aforementioned complex to pass through the solid phase carrier.

In the present invention, the aforementioned complex bound to a solid phase carrier may be separated and recovered from luminescent probe not bound to the target particle by preliminarily adding the solid phase carrier to a solution together with the target particle, luminescent probe and separation probe in (a), and then forming a complex containing the target particle bound to the solid phase carrier, luminescent probe and separation probe and subsequently subjecting the complex to solid-liquid separation treatment in (b). In addition, in (a), a solution may also be prepared by adding a separation probe preliminarily bound to the solid phase carrier, a target particle and a luminescent probe. Furthermore, the separation probe used at this time may be reversibly or irreversibly bound to the solid phase carrier.

A solution containing a complex bound to the solid phase carrier is prepared by adding a suitable solvent to the recovered solid phase carrier. A solution containing this is used in (d). There are no particular limitations on the solvent provided it is a solvent that does not impair detection of light released from the luminescent probe in a subsequent, and can be suitably selected from among buffers commonly used in the art. Examples of such buffers include Tris buffers and phosphate buffers such as phosphate-buffered saline (PBS, pH 7.4).

The recovered solid phase carrier may be washed with a suitable solvent prior to (d). Free luminescent probe can be separated and removed from the complex bound to the solid phase carrier more rigorously as a result of this washing. There are no particular limitations on the solvent used to wash the solid phase carrier provided it is that which does not impair binding between the complex and solid phase carrier, and may be of the same type or different type from the solvent used to prepare the solution containing complex bound to the solid phase carrier in (d).

Subsequently, the aforementioned luminescent probe is dissociated from the complex recovered in (c), and the free luminescent probe and the target particles are separated and individually recovered in (d). The recovered free luminescent probe is used as a sample for measurement using a single molecule optical detection technology such as the scanning molecule counting method in a subsequent operation. In addition, the recovered target particle is again bound with a new luminescent probe in a subsequent operation.

There are no particular limitations on the method used to dissociate the luminescent probe in the complex provided it is a method that is able to eliminate binding between the target particle and luminescent probe in the complex.

For example, in the case the target particle is an oligonucleotide composed of a nucleic acid molecule or a nucleic acid-like substance, and the site in the luminescent probe that binds to the target particle is an oligonucleotide composed of nucleic acid molecule or a nucleic acid-like substance that hybridizes with the target particle, binding between the luminescent probe and the target particle can be eliminated and the luminescent probe can be dissociated from the aforementioned complex by sufficiently raising the temperature of a solution containing the aforementioned complex to a temperature higher than the specific association conditions of the target particle and luminescent probe, or sufficiently lowering the salt concentration of a solution containing the aforementioned complex below the salt concentration of the specific association conditions of the target particle and luminescent probe.

In the case the complex recovered in (c) contains a target particle, luminescent probe and separation probe, the luminescent probe may be dissociated from the complex by eliminating only binding between the target particle and luminescent probe in the complex in (d). As a result of maintaining binding between the target particle and separation probe, the target particle can be separated and recovered from free luminescent probe while in the form of a complex bound to the separation probe. This applies similarly to the case in which the complex recovered in (c) contains target particle, luminescent probe and separation probe and is bound to a solid phase carrier.

For example, in the case the target particle is an oligonucleotide composed of a nucleic acid molecule or a nucleic acid-like substance, and the site that binds with target particle in the luminescent probe and separation probe is also an oligonucleotide composed of a nucleic acid molecule or a nucleic acid-like substance that hybridizes with the aforementioned target particle, the luminescent probe and separation probe may be designed so that the Tm value of the complex of target particle and separation probe is higher than the Tm value of the complex of the target particle and luminescent probe. In this case, the luminescent probe can be dissociated from the target particle while maintaining binding between the target particle and separation probe by using a temperature that is higher than the Tm value of the complex of the target particle and luminescent probe but lower than the Tm value of the complex of the target particle and separation probe.

An example of a method used to make the Tm value of the complex of the target particle and separation probe higher than the Tm value of the complex of the target particle and luminescent probe consists of using a naturally-occurring oligonucleotide having a luminescent substance bound thereto for the luminescent probe, and using an oligonucleotide containing in at least a portion thereof a nucleic acid-like substance capable of forming stronger base pairs than the naturally-occurring nucleotide for the region in the separation probe that binds to the target particle. Examples of nucleic acid-like substances capable of demonstrating more stable binding than naturally-occurring nucleotides include BNA and PNA.

The luminescent probe may be a naturally-occurring oligonucleotide having a luminescent substance bound thereto, and the separation probe may be an oligonucleotide composed of PNA. This is because PNA does not have a negative charge, and even in the case salt concentration in a solution is so low that naturally-occurring oligonucleotides have difficulty in forming an association product, there are cases in which an oligonucleotide composed of PAN is able to bind with a naturally-occurring oligonucleotide and form an association product. Therefore, in the case the target particle is a naturally-occurring oligonucleotide, and in the case a naturally-occurring oligonucleotide having a luminescent substance bound thereto is used for the luminescent probe and an oligonucleotide composed of PNA is used for the separation probe, the luminescent probe can easily be dissociated from the target particle bound to the separation probe by lowering the salt concentration in the solution or removing salt from the solution after having formed a complex of the target particle, luminescent probe and separation probe.

In addition, in the case of using a naturally-occurring oligonucleotide for the region that binds to target particle in both a luminescent probe and separation probe, another example of a method that can be employed consists of sufficiently making the length of the region in the separation probe that binds to the target particle greater than that of the region that binds to the target particle, or increasing the GC content of the region in the separation probe that binds to the target particle to a greater degree than the region that binds to the target particle; so that the Tm values of each region are mutually significantly different.

At least one covalent bond can be formed, prior to (d), between the target particle and the separation probe in the complex formed in (b). As a result of crosslinking the target particle and separation probe by covalent bonding, binding between the target particle and separation probe in subsequent operations can be stabilized and the luminescent probe can be easily dissociated from the complex. In the case of having formed a covalent bond, the luminescent probe can be dissociated while maintaining binding between the target particle and separation probe by, for example, washing the complex containing the target particle, luminescent probe and separation probe under severely stringent solution conditions to the extent that the luminescent probe is no longer able to completely hybridize with the target particle. The formation of a covalent bond between the target particle and separation probe may be carried out before (c) or after (c).

There are no particular limitations on the method used to form a covalent bond provided it allows the formation of a covalent bond that links two single-stranded nucleic acid molecules forming base pairs, and can be suitably selected from among known techniques used when crosslinking nucleic acid molecules. In the present invention, a covalent bond may be formed by a photochemical reaction. A photochemical reaction refers to a reaction carried out by utilizing light energy generated by irradiating with light of a specific wavelength. Since the method used to form a covalent bond by a photochemical reaction is able to form a covalent bond between the nucleic acid chains of a double-stranded nucleic acid molecule by irradiating a solution with light of a specific wavelength, it is not necessary to alter the composition or other conditions of the solution. Consequently, effects on the complex in the solution other than that affecting covalent bond formation can be suppressed and the procedure is simple.

For example, a covalent bond can be formed through a photoreactive base derivative between a target particle and a separation probe by a photochemical reaction by using a separation probe in which at least one base in the region that binds to the target particle is substituted for that photoreactive base derivative. There are no particular limitations on the base substituted for the photoreactive base derivative in the separation probe provided it is a base present in a region that hybridizes with the target particle. In addition, only one base may be substituted for the photoreactive base derivative or two or more bases may be substituted for the photoreactive base derivative.

Here, a photoreactive base derivative refers to a base derivative capable of forming a nucleic acid chain in the same manner as a naturally-occurring nucleotide that has a site where reactivity in an organic synthesis reaction is activated as a result of irradiating with light of a specific wavelength (photoreactive site).

Examples of such photoreactive base derivatives include those in which psoralen has been added to thymine (T) or adenine (A) through a linker (see, for example, Proc. Natl. Acad. Sci. U.S.A., Vol. 88, pp. 5602-5606, July 1991). For example, after having formed a complex containing target particle, luminescent probe and separation probe using a photoreactive base derivative obtained by adding psoralen to T or A through a linker in the region of the separation probe that binds to the target particle, crosslinking occurs between the target particle and separation probe that form base pairs through this psoralen when the complex is irradiated with near ultraviolet light at 254 nm and the like.

In addition, in the case the complex recovered in (c) contains a target particle, luminescent probe and separation probe and is bound to a solid phase carrier, by dissociating the luminescent probe from the complex and subjecting to solid-liquid separation treatment, free luminescent probe and the complex containing the target particle and separation probe and bound to the solid phase carrier can be separated and recovered. The separated and recovered complex bound to the solid phase carrier may be washed with a suitable buffer and the like prior to using in the next operation.

Next, the following operations are carried out as (a') to (d'): (a') preparing a solution obtained by newly adding a luminescent probe to the target particle recovered by separating from free luminescent probe in (d) (or a complex containing a separation probe and target particle in the case of using a separation probe); (b') forming a complex by allowing the aforementioned target particle and luminescent probe to bind in the solution; (c') separating luminescent probes not bound to the target particle, thereby recovering the complex; and, (d') dissociating the luminescent probe from the recovered complex followed by mutually separating and recovering the free luminescent probe and target particles. These operations (a') to (d') can be carried out in the same manner as the previously described (a) to (d).

Operations (a') to (d') may be repeated at least once. In theory, an amount of luminescent probe is recovered in (d') that is equal to the amount of luminescent probe recovered in (d) each time (a') to (d') are carried out. In other words, by repeating (a') to (d'), the amount of luminescent probe recovered can be increased by a factor equal to the number of times these operations are repeated.

The total amounts of free luminescent probes recovered in (d) and (d') are combined for use as a single measurement sample solution, which is then used in measurement using a single molecule optical detection technology such as the scanning molecule counting method. Since the effect of increasing signal sensitivity is obtained by repeating (a') to (d'), the volume of the single measurement sample solution containing the total amount of free luminescent probe recovered in (d) and (d') may be roughly equal to the volume of the solution of the free luminescent probes recovered in (d).

For example, by dissociating luminescent probe from the complex containing target particle and luminescent probe in each (d') in a solution containing the free luminescent probes recovered in (d), the free luminescent probes are recovered in the same solution in all of (d) and (d'). More specifically, after having added a solution containing free luminescent probes recovered in (d) to the complex recovered in (c'), the luminescent probe is dissociated from the complex in the solution followed by mutually separating and recovering the free luminescent probes and target particles in (d').

In addition, in the case of respectively and individually recovering free luminescent probes in the form of a solution in each (d'), by mixing all of the solutions and carrying out concentration treatment using a method such as freeze-drying that does not impair luminescence from the luminescent probe, the volume of the single measurement sample solution containing the total amount of free luminescent probes recovered in (d) and (d') can be made to be roughly equal to the volume of the solution of free luminescent probes recovered in (d).

Subsequently, the number of molecules of the aforementioned luminescent probe in the resulting measurement sample solution is calculated using a method by which light emitted from the aforementioned luminescent probe in the photodetection region of an optical system of a confocal microscope or multi-photon microscope is detected while moving the location of the photodetection region using the optical system of the confocal microscope or multi-photon microscope. In other words, in the detection method of the present invention, a target particle is detected indirectly by detecting a luminescent probe that has been dissociated by going through a prescribed treatment after having been temporarily bound to the target particle.

In the present invention and description of the present application, a "photodetection region" of the optical system of a confocal microscope or multi-photon microscope refers to a microregion in which light is detected in those microscopes, and in the case illumination light is imparted from an object lens, the region where that illumination light is focused corresponds to a microregion. Furthermore, this microregion is defined by the positional relationship between the object lens and pinhole in a confocal microscope in particular.

A luminescent probe in a measurement sample solution can be detected by detecting the optical properties of light emitted from the luminescent probe when irradiated with light of a wavelength optimal for the spectral properties thereof. Furthermore, "detecting the optical properties of a luminescent probe" refers to detecting an optical signal of a specific wavelength emitted from the luminescent probe. Examples of the optical signal include fluorescence intensity and fluorescence polarization.

In the detection method of the present invention, the number of molecules of a luminescent probe in a measurement sample solution is counted with the scanning molecule counting method.

In the scanning molecule counting method, since each particle dispersed or dissolved in a solution is detected individually, counting of particles, determination of particle concentration or number density in a measurement sample solution, or acquisition of information relating to concentration or number density, can be carried out quantitatively using that information. Namely, according to the scanning molecule counting method, since a particle is detected one at a time by creating a 1:1 correlation between a particle passing through a photodetection region and a detected optical signal, particles dispersed and moving randomly in a solution can be counted, and the concentration or number density of particles in a measurement sample solution can be determined more accurately than in the prior art. For example, in the case of detecting free luminescent probe in the detection method of the present invention using the scanning molecule counting method, and determining particle concentration by individually detecting particles in a measurement sample solution and counting the number of particles based on light emitted from a luminescent probe, the luminescent probe can be detected even if the concentration of the luminescent probe in the measurement sample solution is lower than a concentration able to be determined based on fluorescence intensity as measured with a fluorescence spectrophotometer or plate reader.

In the case of single molecule measurement or other forms of highly sensitive measurement, and particularly in the case of the scanning molecule counting method, there are cases in which detection accuracy is low for luminescent particles in which diffusion movement in a solution in the manner of a solid phase carrier and the like is comparatively slow. In the present invention, as a result of targeting detection on a luminescent probe in a free state that has been separated from a solid phase carrier during measurement according to the scanning molecule counting method, even in the case of using a fluorescent single molecule measurement method, the luminescent probe can be detected with high accuracy by removing the effects of the solid phase carrier.

Figure 1:
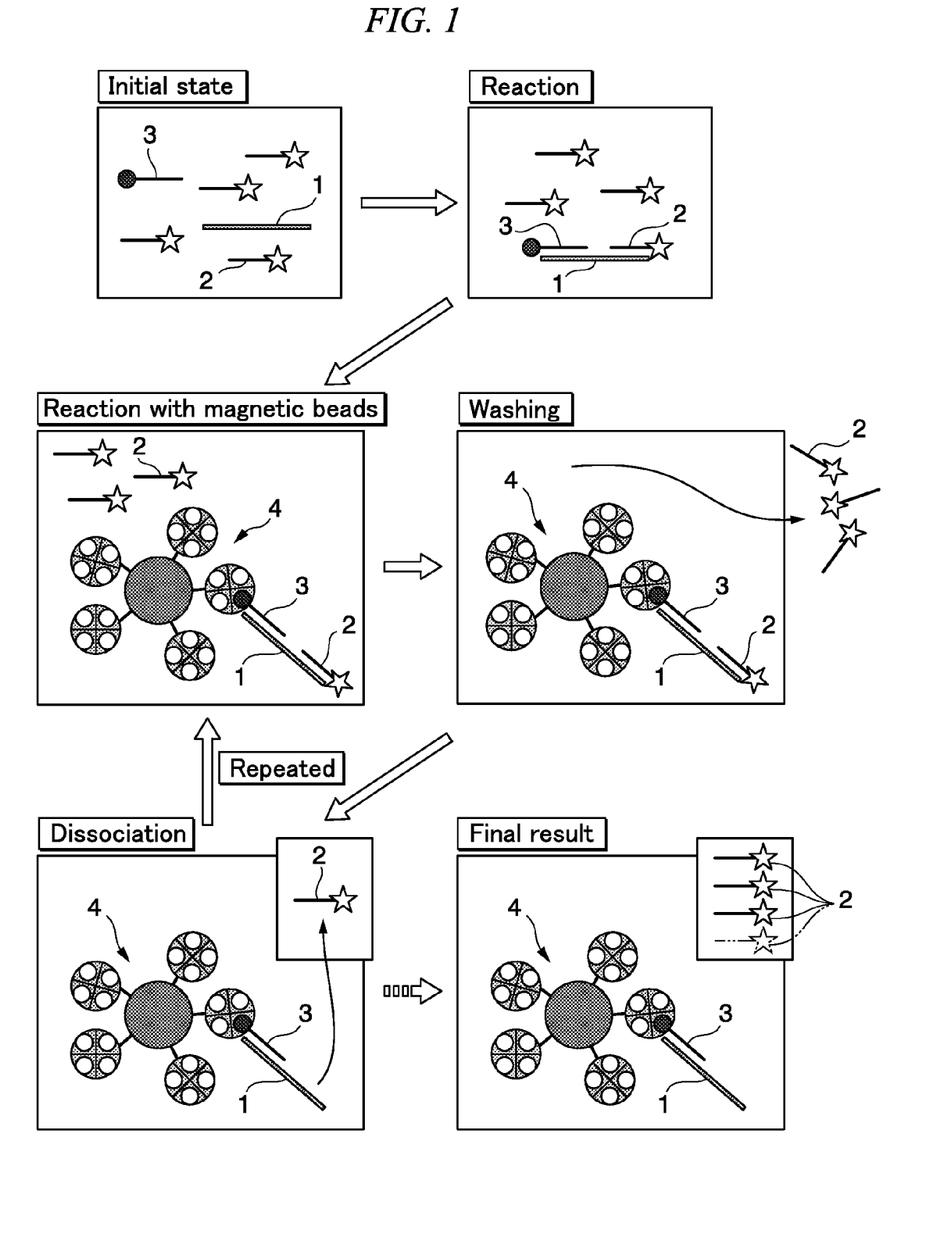
FIG. 1 is a drawing schematically showing one aspect of the method for detecting a target particle of the present invention.

FIG. 1 is a drawing schematically showing an aspect of the detection method of the present invention that uses a separation probe and a solid phase carrier that binds to the separation probe. First, a target particle 1, a luminescent probe 2, and a separation probe 3 are combined to form a complex. After binding the complex to a solid phase carrier 4 using the separation probe 3 and removing free luminescent probe 2 by washing, the luminescent probe 2 is dissociated from the complex, and the luminescent probe 2 and the target particle 1 bound to the solid phase carrier 4 through the separation probe 3 are separated and recovered. Subsequently, a new luminescent probe 2 is added to the recovered complex containing the target particle 1, and after combining with the target particle 1 in the complex and washing, the luminescent probe 2 is again dissociated, and the free luminescent probe 2 and the target particle 1 bound to the solid phase carrier 4 through the separation probe 3 are separated and recovered. A plurality of luminescent probes 2 are recovered from a single molecule of the target particle 1 by repeating these operations.

EXAMPLES

Although the following provides a more detailed explanation of the present invention by indicating examples thereof, the present invention is not limited to the following examples.

Reference Example 1

An experiment was conducted to demonstrate that a higher signal is obtained for a target particle during measurement according to the scanning molecule counting method in the case of using a plurality of types of luminescent probes than in the case of using one type of luminescent probe.

A polynucleotide composed of the base sequence shown in SEQ ID NO: 1 (to be referred to as Target Nucleic Acid Molecule 1) was used for the target particle, oligonucleotides composed of the base sequences shown in SEQ ID NOS: 2 to 5 and having a fluorescent substance in the form of ATTO® 647N (ATTO-TEC Gmbh) bound to the 5'-terminal thereto (Probes 1 to 4) were used as luminescent probes, and an oligonucleotide composed of the base sequence indicated in SEQ ID NO: 6 and having biotin bound to the 3'-terminal thereof (Biotinated Probe 1) was used for the separation probe. Each of the base sequences are shown in Table 1. In the Target Nucleic Acid Molecule 1, underlines indicate those regions that bind to the luminescent probes and biotinated probe, respectively. Furthermore, the Target Nucleic Acid Molecule 1, Luminescent Probes 1 to 4 and Biotinated Probe 1 are all polynucleotides composed of naturally-occurring nucleotides.

TABLE 1

|  | Base Sequence | SEQ ID NO: |
|---|---|---|
| Target Nucleic Acid Molecule 1 | GACTGAATATAAACTTGTGGA GCCTGGGAAAGTC CCCTCAACTATGGGAGCCAGTGTGGACAAATCA GGGAGCAGCCAGTCTTAACCATGAAAAACAGAC TAGC | 1 |
| Luminescent Probe 1 | ATTO 647N-AGTTGAGGGGACTTTCCCAGGC | 2 |
| Luminescent Probe 2 | ATTO 647N-TGTCCACACTGGCTCCCA | 3 |
| Luminescent Probe 3 | ATTO 647N-AAGACTGGCTGCTCCCTGAT | 4 |
| Luminescent Probe 4 | ATTO 647N-GCTAGTCTGTTTTTCATGGT | 5 |
| Biotinated Probe 1 | CCACAAGTTTATATTCAGTC-Biotin | 6 |

Sample Solution 1 (100 μL) was prepared using Tris buffer (10 mM Tris-HCl, 400 mM NaCl, 0.05% Triton X-100) so that the concentration of the target nucleic acid molecule was 1 pM, the concentration of Luminescent Probe 1 was 800 pM, the concentration of Biotinated Probe 1 was 200 pM, and the concentration of Poly(deoxyinosinic-deoxycytidylic) acid (Sigma-Aldrich Corp.) was 0.1 U/mL (where, 1 U represents an amount that yields absorbance of 1.0 at 260 nm in water (optical path length: 1 cm)). In addition, Sample Solution 2 was prepared in the same manner as the aforementioned Sample Solution 1 with the exception of preparing so that the concentrations of Luminescent Probes 1, 2, 3 and 4 were each 200 pM (total: 800 pM). Moreover, Control Sample Solutions 1 and 2 were also prepared in the same manner as Sample Solution 1 and Sample Solution 2, respectively, with the exception of not containing the Target Nucleic Acid Molecule 1.

The sample solutions were heated for 5 minutes at 95° C. followed by lowering the liquid temperature to 25° C. at a rate of 0.1° C./minute. 1 μL of 0.1% bovine serum albumin (BSA) was added followed by the addition of streptavidin-coated magnetic beads (Catalog No. 650-01, Invitrogen Corp.) and allowing to react while shaking for 90 minutes at 25° C. Continuing, after washing the magnetic beads preset in the sample solutions three times with 500 μL of wash buffer (10 mM Tris-HCl, 400 mM NaCl, 0.05% Triton X-100) using a magnet, 100 μL of elution buffer (10 mM Tris-HCl, 0.05% Triton X-100) were added followed by heating for 30 seconds at 95° C. and then rapidly cooling over ice. After gathering the magnetic beads against the inner wall of the container using a magnet, the supernatant was recovered and the number of molecules of luminescent probe contained in the sample solutions was measured according to the scanning molecule counting method.

The MF20 Single Molecule Fluorescence Spectroscopy System (Olympus Corp.) equipped with the optical system of a confocal fluorescent microscope and a photon counting system was used as an optical analysis device during measurement. Chronological photon count data was acquired for the aforementioned supernatant. At that time, laser light having a wavelength of 642 nm and irradiated at 1 mW was used as excitation light, and the detecting light wavelength was set to 660 nm to 710 nm using a band pass filter. The movement speed of the location of the photodetection region in the sample solutions was set to 90 mm/sec, BIN TIME was set to 10 μs, and measurement time was set to 2 seconds. In addition, measurements were carried out five times each followed by calculation of their mean and standard deviation. Following measurement of light intensity, optical signals detected in chronological data were counted from chronological photon counting data acquired for each supernatant. During data smoothing according to the moving average method, the number of data points averaged at one time was set to 11, and moving average processing was repeated five times. In addition, during fitting, a Gaussian function was fit to the chronological data using the least squares method, and peak intensity, peak width (half width maximum) and correlation coefficient (in the Gaussian function) were determined. During processing for evaluating the peaks, only those peak signals that satisfied the following conditions were judged to be an optical signal corresponding to a luminescent probe:

20 μsec<peak width<400 μsec;

peak intensity>1 (photons/10 μsec); and, correlation coefficient>0.90 while on the other hand, peak signals not satisfying the aforementioned conditions were ignored as noise, and the number of signals judged to be optical signals corresponding to a luminescent probe was counted as the "number of peaks".

Figure 2:
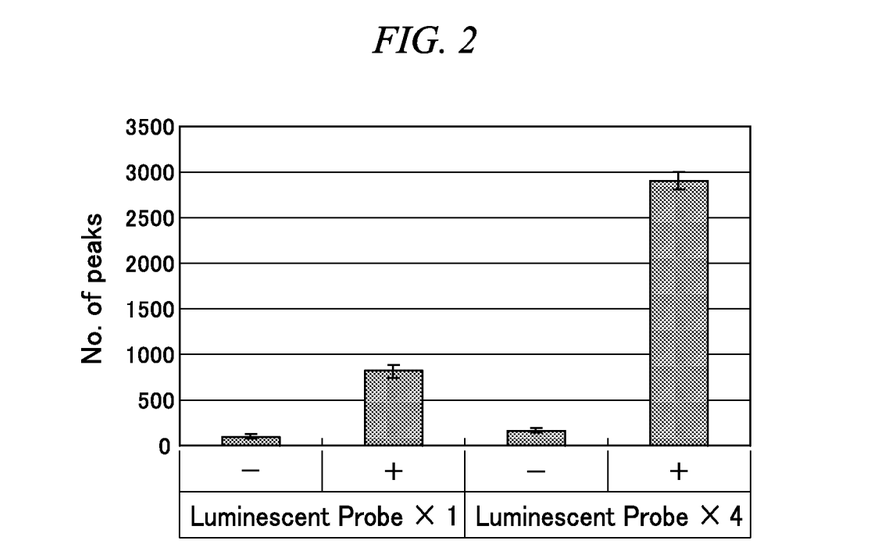
FIG. 2 is a drawing indicating the results of counting the number of peaks of each sample solution in Reference Example 1.

The results of counting the number of peaks of each sample solution are shown in FIG. 2. In the drawing, "Luminescent Probe×1(−)" indicates the result for Control Sample Solution 1 using one type of luminescent probe but not containing Target Nucleic Acid Molecule 1, "Luminescent Probe×1(+)" indicates the result for Sample Solution 1 using one type of luminescent probe and containing Target Nucleic Acid Molecule 1, "Luminescent Probe×4(−)" indicates the result for Control Sample Solution 2 using four types of luminescent probes but not containing Target Nucleic Acid Molecule 1, and "Luminescent Probe×4(+)" indicates the result for Sample Solution 2 using four types of luminescent probes and containing Target Nucleic Acid Molecule 1. In comparison with the case of using one type of luminescent probe, the signal was about 3.8 times higher in the case of using four types of luminescent probes (signal: (number of peaks in the presence of Target Nucleic Acid Molecule 1)−(number of peaks in the absence of Target Nucleic Acid Molecule 1)). This is thought to be the result of a plurality of signal sources having been generated from a single target nucleic acid molecule due to having dissociated luminescent probes from the Target Nucleic Acid Molecule 1 after having bound a plurality of luminescent probes to the Target Nucleic Acid Molecule 1 and removing free luminescent probe by washing.

Example 1

The effect of the number of repetitions of operations (a') to (d') in the detection method of the present invention on detection sensitivity of a target particle was investigated by setting the number of repetitions of the operations to 0 times, 1 time or 2 times.

Naturally-occurring polynucleotide composed of the base sequence indicated in SEQ ID NO: 7 (to be referred to as Target Nucleic Acid Molecule 2) was used for the target particle, Luminescent Probe 1 used in Reference Example 1 was used for the luminescent probe, and an oligonucleotide composed of the base sequence indicated in SEQ ID NO: 8 and having biotin bound to the 3'-terminal thereof (Biotinated Probe 2) was used for the separation probe. The base sequences of the Target Nucleic Acid Molecule 2 and Biotinated Probe 2 are shown in Table 2. In the Target Nucleic Acid Molecule 2, underlines indicate those regions that bind to the Luminescent Probe 1 and Biotinated Probe 2, respectively. In addition, the base sequence of the PNA of the Biotinated Probe 2 is shown after substituting for the naturally-occurring polynucleotide corresponding to PNA.

TABLE 2

| | Base Sequence | SEQ ID NO: |
|---|---|---|
| Target Nucleic Acid Molecule 2 | GACTGAATATAAACTTGTGGA GCCTGGGAAAGTC CCCTCAACT | 7 |
| Biotinated Probe 2 | CCACAAGTTTATATTCAGTC-Biotin | 8 |

First, three sample solutions (100 μL) (Sample Solutions A to C) were prepared using Tris buffer (10 mM Tris-HCl, 400 mM NaCl, 0.05% Triton X-100) so that the concentration of Target Nucleic Acid Molecule 2 was 1 pM, the concentration of Luminescent Probe 1 was 200 pM, the concentration of Biotinated Probe 2 was 200 pM, and the concentration of Poly(deoxyinosinic-deoxycytidylic) acid (Sigma-Aldrich Corp.) was 0.1 U/mL. In addition, three control sample solutions (Control Sample Solutions A to C) were prepared in the same manner as Sample Solution 1 with the exception of not containing the Target Nucleic Acid Molecule 2.

The sample solutions were heated for 5 minutes at 95° C. followed by lowering the liquid temperature to 25° C. at a rate of 0.1° C./minute. 1 μL of 0.1% bovine serum albumin (BSA) was added followed by the addition of streptavidin-coated magnetic beads (Catalog No. 650-01, Invitrogen Corp.) and allowing to react while shaking for 90 minutes at 25° C. Continuing, after washing the magnetic beads in the sample solutions three times with 500 μL of wash buffer (10 mM Tris-HCl, 400 mM NaCl, 0.05% Triton X-100) using a magnet, 100 μL of elution buffer (10 mM Tris-HCl, 0.05% Triton X-100) were added followed by incubating for 5 minutes at 50° C. Next, after gathering the magnetic beads against the inner wall of the container using a magnet, the supernatant was recovered. The recovered supernatant was designated as "Supernatant 1", while the magnetic beads gathered on the inner wall of the container were designated as "Magnetic Beads 1". The procedure was terminated at this point for Sample Solution A and Control Sample Solution A, and the resulting Supernatant 1 was used as a measurement sample solution for measurement according to the scanning molecule counting method. The procedure proceeded to the following operations for Sample Solutions B and C and Control Sample Solutions B and C.

Next, a solution (100 μl) prepared using the aforementioned Tris buffer so that the concentration of Luminescent Probe 1 was 200 pM, the concentration of Poly(deoxyinosinic-deoxycytidylic) acid (Sigma-Aldrich Corp.) was 0.1 U/mL and the concentration of BSA was 0.001% was added to and mixed with Magnetic Beads 1, and the resulting sample solution was allowed to react while shaking for 1 hour at 25° C. Continuing, after washing the magnetic beads in the sample solution three times with 500 μL of the aforementioned wash buffer using a magnet, the aforementioned Supernatant 1 was added followed by incubating for 5 minutes at 50° C. Next, after gathering the magnetic beads against the inner wall of the container using a magnet, the supernatant was recovered. The recovered supernatant was designated as "Supernatant 2", while the magnetic beads gathered on the inner wall of the container were designated as "Magnetic Beads 2". The procedure was terminated at this point for Sample Solution B and Control Sample Solution B, and the resulting Supernatant 2 was used as a measurement sample solution for measurement according to the scanning molecule counting method. The procedure proceeded to the following operations for Sample Solution C and Control Sample Solutions C.

Next, a solution (100 μl) prepared using the aforementioned Tris buffer so that the concentration of Luminescent Probe 1 was 200 pM, the concentration of Poly(deoxyinosinic-deoxycytidylic) acid (Sigma-Aldrich Corp.) was 0.1 U/mL and the concentration of BSA was 0.001% was added to and mixed with Magnetic Beads 2, and the resulting sample solution was allowed to react while shaking for 1 hour at 25° C. Continuing, after washing the magnetic beads in the sample solution three times with 500 μL of the aforementioned wash buffer using a magnet, the aforementioned Supernatant 2 was added followed by incubating for 5 minutes at 50° C. Next, after gathering the magnetic beads against the inner wall of the container using a magnet, the supernatant was recovered. The recovered supernatant was designated as "Supernatant 3", while the magnetic beads gathered on the inner wall of the container were designated as "Magnetic Beads 3". The procedure was terminated at this point, and the resulting Supernatant 3 was used as a measurement sample solution for measurement according to the scanning molecule counting method.

Figure 3:
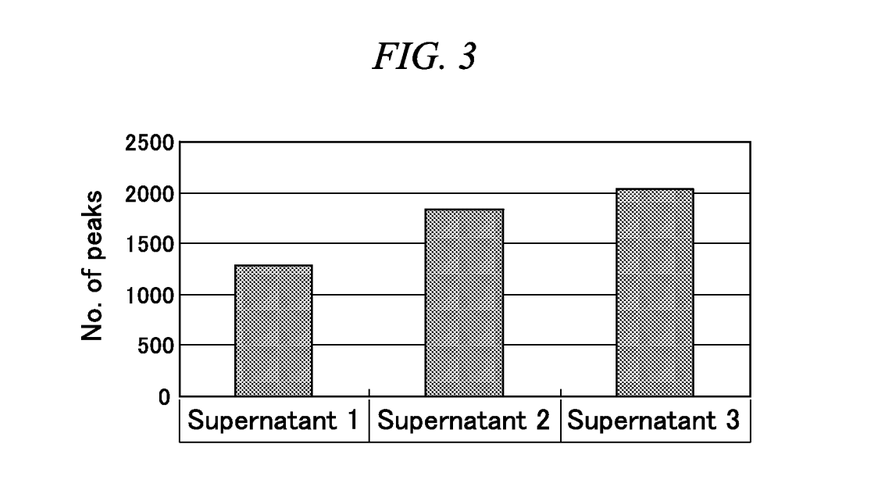
FIG. 3 is a drawing showing the results of counting the number of peaks obtained by subtracting the number of peaks of a measurement sample solution prepared from a reference sample solution (number of peaks in the absence of target particles) from the number of peaks of a measurement sample solution prepared from a sample solution (number of peaks in the presence of target particles).

The number of molecules of Luminescent Probe 1 in the resulting measurement sample solutions (Supernatants 1 to 3) was measured according to the scanning molecule counting method. Measurement was carried out in the same manner as Reference Example 1 with the exception of changing the measurement time to 20 seconds. The results of counting the number of peaks of each measurement sample solution are shown in FIG. 3. In FIG. 3, "Supernatant 1" to "Supernatant 3" respectively indicate the number of peaks obtained by subtracting the number of peaks of measurement sample solutions prepared from control sample solutions (number of peaks in the absence of target particles) from the number of peaks of measurement sample solutions prepared from sample solutions (number of peaks in the presence of target particles). As a result, the number of peaks was greater for Supernatant 2 than Supernatant 1 and was greater for Supernatant 3 than Supernatant 2. In other words, the resulting number of peaks was confirmed to increase dependent upon the number of times operations (a') to (d') of the present invention were repeated. On the basis of these results, the detection method of the present invention was clearly determined to result in the generation of a plurality of signal sources from a single molecule of target particle, and accordingly shorten the detection time or further enhance the detection sensitivity of target particles in comparison with the prior art.

The invention claimed is:

1. A method for indirectly detecting a particle dispersed and moving randomly in a solution using a luminescent probe, comprising:
   (a) preparing a solution containing a target particle to be detected and a first luminescent probe that directly or indirectly binds to the target particle;
   (b) forming a complex containing the target particle and the first luminescent probe in the solution;
   (c) removing first luminescent probes not bound to the target particles from the solution containing the complex, thereby recovering the complex;
   (d) dissociating the first luminescent probe from the recovered complex and separately separating the free first luminescent probe and the target particle, thereby separately recovering the free first luminescent probe and the target particle;
   (e) repeating one or more times a cycle consisting of the following operations (a') to (d'):
      (a') preparing a solution by adding a second luminescent probe to the target particle recovered by separating from the free first luminescent probe in the (d);
      (b') forming a complex containing the target particles and the second luminescent probe in the solution following the (a');
      (c') separating second luminescent probes not bound to the target particle, thereby recovering the complex from the solution following the (b'); and,
      (d') dissociating the second luminescent probe from the complex recovered in the (c') followed by mutually separating and recovering free second luminescent probes and the target particle;
   followed by preparing a single measurement sample solution containing the total amount of the free first and second luminescent probes recovered in the (d) and the (d'); and,
   (f) calculating the number of molecules of the first and second luminescent probes in the measurement sample solution by a method consisting of detecting light emitted from the first and second luminescent probes in a photodetection region of an optical system of a confocal microscope or multi-photon microscope while moving the location of the photodetection region in the measurement sample solution using the optical system.

2. The method for detecting a target particle according to claim 1, wherein dissociation of the second luminescent probe from the complex in the (d') is carried out in a solution containing the free first luminescent probes recovered in the (d).

3. The method for detecting a target particle according to claim 1, wherein after mixing the entirety of the solutions containing the free first and second luminescent probes recovered in each of the (d) and the (d'), a single measurement sample solution is prepared by carrying out concentration treatment.

4. The method for detecting a target particle according to claim 1, wherein a separation probe that binds to the target particle independent of the first luminescent probe is further added to the solution in the (a),
   a complex formed in the (b) contains the target particle, the first luminescent probe and the separation probe, and a complex formed in the (b') contains the target particle, the second luminescent probe and the separation probe,
   the target particle in the state of a complex bound to the separation probe in the (d) is recovered by separating from the free first luminescent probes, and the target particle in the state of a complex bound to the separation probe in the (d') is recovered by separating from the free second luminescent probes.

5. The method for detecting a target particle according to claim 1, wherein the target particle is a nucleic acid molecule.

6. The method for detecting a target particle according to claim 4, wherein the target particle is a nucleic acid molecule, and the Tm value of a complex of the target particle and the separation probe is higher than the Tm value of a complex of the target particle and the first and second luminescent probes.

7. The method for detecting a target particle according to claim 6,
   wherein dissociation of the first luminescent probe from the complex is carried out in the (d) by making the temperature of a solution containing the complex higher than the Tm value of a complex of the target particle and the first luminescent probe and lower than the Tm value of a complex of the target particle and the separation probe, and wherein dissociation of the second luminescent probe from the complex is carried out in the (d') by making the temperature of a solution containing the complex higher than the Tm value of a complex of the target particle and the second luminescent probe and lower than the Tm value of a complex of the target particle and the separation probe.

8. The method for detecting a target particle according to claim 4, wherein the first and second luminescent probes are naturally-occurring oligonucleotides having a luminescent substance bound thereto, and the separation probe is an oligonucleotide composed of peptide nucleic acids.

9. The method for detecting a target particle according to claim 4, wherein forming of at least one covalent bond between the target particle and the separation probe in the complex formed in the (b) is carried out prior to the (d).

10. The method for detecting a target particle according to claim 4, wherein recovery of the complex in the (c), recovery of the free first luminescent probes in the (d) and recovery of the free second luminescent probes in the (d') are carried out by solid-liquid separation treatment using a solid phase carrier that directly or indirectly binds to the separation probe.

11. The method for detecting a target particle according to claim 1, wherein the first luminescent probe of the (a) is two or more different luminescent probes.

* * * * *

SEQUENCE LISTING

<160> NUMBER OF SEQ ID NOS: 8

<210> SEQ ID NO 1
<211> LENGTH: 104
<212> TYPE: DNA
<213> ORGANISM: Artificial Sequence
<220> FEATURE:
<223> OTHER INFORMATION: Description of Artificial Sequence: Target
      nucleic acid molecule1.

<400> SEQUENCE: 1
gactgaatat aaacttgtgg agcctgggaa agtcccctca actatgggag ccagtgtgga    60
caaatcaggg agcagccagt cttaaccatg aaaaacagac tagc                    104

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Luminescent
      probe1.

<400> SEQUENCE: 2
agttgagggg actttcccag gc                                             22

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Luminescent
      probe2.

<400> SEQUENCE: 3
tgtccacact ggctccca                                                  18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Luminescent
      probe3.

<400> SEQUENCE: 4
aagactggct gctccctgat                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Luminescent
      probe4.

<400> SEQUENCE: 5
gctagtctgt ttttcatggt                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Biotin-
      binding probe1.

<400> SEQUENCE: 6

```
ccacaagttt atattcagtc                                                    20

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence:
      Target nucleic acid molecule2.

<400> SEQUENCE: 7
gactgaatat aaacttgtgg agcctgggaa agtcccctca act                          43

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: DNA
      sequence corresponding to PNA sequence of Biotin-binding probe2.

<400> SEQUENCE: 8
ccacaagttt atattcagtc                                                    20
```